United States Patent [19]

Birkmayer

[11] Patent Number: 5,332,727
[45] Date of Patent: Jul. 26, 1994

[54] STABLE, INGESTABLE AND ABSORBABLE NADH AND NADPH THERAPEUTIC COMPOSITIONS

[75] Inventor: Joerg G. D. Birkmayer, Vienna, Austria

[73] Assignee: Birkmayer U.S.A., New York, N.Y.

[21] Appl. No.: 55,049

[22] Filed: Apr. 29, 1993

[51] Int. Cl.⁵ .................. A61K 31/70; A61K 37/48; A61K 37/50
[52] U.S. Cl. ................... 514/52; 424/94.1; 424/94.4; 514/959
[58] Field of Search .......... 514/52, 960, 961; 424/94.1, 464, 465, 474, 475, 477, 94.4

[56] References Cited

U.S. PATENT DOCUMENTS

| | | | |
|---|---|---|---|
| 3,728,445 | 4/1973 | Bardani | 424/22 |
| 4,438,091 | 4/1984 | Gruber | 424/21 |
| 4,970,200 | 11/1990 | Birkmayer et al. | 514/52 |
| 5,019,561 | 5/1981 | Birkmayer | 514/52 |
| 5,055,304 | 10/1991 | Makino et al. | 424/465 |
| 5,135,757 | 8/1992 | Baichwal | 424/465 |

OTHER PUBLICATIONS

Lieberman et al: Pharmaceutical Dosage Forms; Tablets vol. 3, Marcel Decker, Fuc, N.Y. (1982) pp. 108–109.

Primary Examiner—Marianne M. Cintins
Assistant Examiner—T. J. Criares
Attorney, Agent, or Firm—Kenyon & Kenyon

[57] ABSTRACT

A stable, ingestable and intestine-absorbable therapeutic composition comprising NADH or NADPH, or physiologically acceptable salts thereof, in a pill form. The pill has an outer surface covered by an acid stable protective coating. This oral form of NADH/NADPH may be taken for a variety of known therapeutic effects.

11 Claims, No Drawings

STABLE, INGESTABLE AND ABSORBABLE NADH AND NADPH THERAPEUTIC COMPOSITIONS

BACKGROUND OF THE INVENTION

1. Field of the Invention

The invention relates to stable NADH and NADPH compositions which may be taken orally as a therapeutic agent.

2. Description of Related Art

Nicotinamide-adenine-dinucleotide in its reduced form ("NADH") and nicotinamide-adenine-phosphate-dinucleotide in its reduced form ("NADPH") are physiological substances which occur in all living cells including human cells. These substances are cofactors for a variety of enzymes, the majority of which catalyze oxidation-reduction reactions. Prior to recent discoveries as to the therapeutic properties of these compounds, their principal utility has been as diagnostic tools in clinical biochemistry and as essential components in the reaction kits, for example, in measuring Lactatdehydrogenase (LDH).

The most important function of NADH is its driving force for cell respiration. When using oxygen, NADH forms water and 3 ATP molecules in accordance with the following formula: $NADH + H^+ + \frac{1}{2}O_2 + 3\ Pi + 3\ ATP \rightarrow NAD^{++} + 3\ ATP + 4H_2O$. Thus, with 1 NADH molecule, 3 ATP molecules are obtained which have an energy of approximately 21 kilocalories. This process is called oxidative phosphorylation. The supply of NADH and/or NADPH makes this work much easier for the organism, because it has greater energy reserves as a result.

More recently, NADH and NADPH and pharmaceutically acceptable salts thereof have been shown to be useful in the treatment of Parkinson's Disease. The effectiveness of these agents for this purpose is documented in my existing U.S. Pat. Nos. 4,970,200 and 5,019,561, the disclosure of which are incorporated herein by reference.

In addition, I have discovered that these substances are effective in the treatment of Morbus Alzheimer (.i-e,, Alzheimer's Disease), as well as in the treatment of mental depression, which is the subject of my co-pending application Ser. No. 07/815,407 filed with the U.S. Patent and Trademark Office on Dec. 31, 1991.

Prior to my recent discoveries, NADH and NADPH have never been considered for therapeutic use, probably because it was believed that these compounds are rather unstable and, hence, not capable of being absorbed by the intestines of the human body. It would have been expected that these substances would be hydrolized in the plasma within a few seconds.

However, studies performed recently using NADH and NADPH demonstrate that these assumptions are incorrect. When NADH and NADPH were applied intravenously to patients with Parkinson's disease, a remarkable beneficial effect was observed which lasted at least 24 hours. See U.S. Pat. Nos. 4,970,200 and 5,019,561. This indicates that NADH and NADPH are not rapidly degraded in the plasma and blood.

One drawback to intravenous application of NADH and NADPH is that it requires an injection which has to be performed in a hospital or at the physician's practice. This requirement can be inconvenient or demanding on the patient's schedule. Therefore, it would be desirable to find a stable oral form for NADH and NADPH which would allow patients to take these substances regularly under their own supervision.

SUMMARY OF THE INVENTION

It is an object of the invention to provide a shelf stable oral form of NADH and NADPH which will allow patients to object of the invention to provide a shelf ingest these substances for their therapeutic effect at their convenience.

It is a further object of the invention to provide such stable oral forms of NADH and NADPH which are able to withstand the acidic conditions of the stomach so that the substances may survive to be absorbed by the intestine.

In accordance with the invention, there is provided a shelf stable pill (e.g., tablet, capsule, microtablet or micropellet form) of NADH and/or NADPH which is coated with an acid stable protective film so that the therapeutic substance can survive the acidic environment of the stomach. In preferred galenic formulations, the NADH and/or NADPH is compressed together with a stabilizer and a filler. It was surprising and totally unexpected to discover that the NADH and/or NADPH taken orally is absorbed by the intestine and the bloodstream where it is transported to the nervous system to have its known therapeutic effect.

DETAILED DESCRIPTION OF THE INVENTION

Both NADH and NADPH are very unstable at pHs below 7 which prevail within the confines of the stomach. Therefore, in accordance with the invention, these substances must be coated with an acid stable protective film so that they can survive the stomach environment for subsequent absorption by the intestine. Suitable acid stable coatings are known in the art and can be applied by a conventional coating process after the active ingredients are formed into a tablet or capsule. Examples of suitable coatings are: cellulose acetate phthalate; polyvinylacetate phthalate; hydroxyl-propyl-methyl cellulose phthalate; metacryllic acid copolymers; fat-wax; shellac; zein; aqua-coating; and surerelease. A preferred coating medium is set forth in Example 1 below. Another possibility for the coating is a solution of a phthalate and a lack dry substance in isopropanol. An example of a suitable lack dry substance is sold under the name EUDRAGIT TM by Rohm Pharma. Alternatively, a protein coating in an aqueous medium may be applied. However, a sugar-coating should not be used because it will destabilize NADH.

Although NADH and/or NADPH may be used by themselves in pure form (they are quite stable in compressed form when protected from light), it is preferred that they be combined in a galenic formulation with a stabilizer, and most preferably with both a stabilizer and a filler. It has been found that the following stabilizers are effective and result in the greatest shelf stability for NADH and NADPH: $NaHCO_3$; ascorbic acid and sodium ascorbate; tocopherols and tocopherolacetates; polyvinylpyrolidone ("PVP") 12 (12 representing the molecular weight 12,000); PVP 25; PVP 40; PVP PF 17 (meaning polymer having a molecular weight from 17,000) and PVP PF 60. NADH/NADPH formulations containing such stabilizers are stable for up to two years. Other various stabilizers will become apparent to those skilled in the art.

Suitable fillers for use with NADH and NADPH include: mannitol, microcrystalline cellulose, carboxymethyl cellulose; and dibasic calcium phosphate. Other suitable fillers will become apparent to those skilled in the art. Lactose should be avoided as a filler because it reacts with NADH.

In general, a preferred formulation will include about 3 to 10% by weight NADH and/or NADPH; about 1 to 10% by weight stabilizer; and the remainder as filler. Such a formulation, after being compressed into a pill and coated, is stable for over 24 months.

The NADH and/or NADPH, together with the optional stabilizer and filler, may be formed into tablets, capsules, microtablets or micropellets by processes known in the art of pill manufacturing. Tablets may be formed either by direct compression or by granulation followed by compression. Capsules may be formed by blending the components and subsequently filling capsules with the blend using conventional automatic filling equipment. Microtablets may be formed by compressing powdered or granulated components into, e.g., 2 mm diameter tablets.

In the case of direct compression into tablets, a particularly preferred formulation is: NADH 5%, sodium ascorbate 5%, magnesium stearate 3%, talc 4%, silicon dioxide 1%, and mannitol 82%.

In the case of capsules, a particularly preferred formulation is: NADH 5%, sodium ascorbate 5%, polyvinylpyrolidone (PVP) 5%, microcrystalline cellulose 77%, magnesium stearate 3%, alpha-tocopherolacetate 1%, talc 3%, and silicon dioxide 1%.

A suitable single dose of NADH and/or NADPH for oral application is 5 to 500 mg, preferably 25 to 100 mg. A suitable daily dose is 5 to 1,500 mg, preferably 25 to 300 mg. Such dosages improve the motor system in Parkinsonian patients.

Suitable physiologically acceptable salts of the coenzymes NADH and NADPH include all known physiologically acceptable acidic and basic salt-forming substances, for example: inorganic acids such as, for example, hydrohalic acids, sulfuric acid, phosphoric acid; organic acids such as, for example, aliphatic or aromatic carboxylic acids, e.g., formic acid, acetic acid, succinic acid, lactic acid, malic acid, tartaric acid, citric acid, maleic acid, phenylacetic acid, benzoic acid, salicylic acid or ascorbic acid; or alkali metal hydroxides or alkaline earth metal hydroxides or salts.

NADH, NADPH or their physiologically compatible salts can be manufactured in the usual manner with pharmaceutically acceptable auxiliaries and carrier materials. If necessary, they can also be used in combination with other active ingredients, for example, postsynaptic dopamine agonists such as Lisuride or Amorphine.

EXAMPLE 1

A therapeutic composition consisting of 5% by weight NADH, 5% by weight poly-(1-vinyl-2-pyrolidone) as a stabilizer, and 90% by weight D-mannitol as a filler was formulated. The mixture was granulated and compressed into 100 mg tablets.

A coating suspension was formed by mixing the following constituents: 0.91 kg cellulose acetate phthalate; 0.05 kg magnesium stearate; 0.28 kg ethyl phthalate; 6.0 kg acetone and 0.03 kg water. Each tablet was then coated with the suspension to form an acid protective film covering the tablet.

The coated tablets were then tested for the amount of time they took to dissolve in a normal stomach environment (i.e., the "dissolution time"). This was done using a dissolution tester ZT 3 instrument from Erweka Company (Germany). Twelve tablets from each lot were moved for 2 hours in 0.1% hydrochloric acid. After this treatment the integrity of the tablets was checked under a microscope. The surface of all tablets appeared fully intact. Thus, it was determined that the dissolution time was at least 2 hours. This time is sufficient to allow for the survival of the NADH through the acidic environment of the stomach so that it may be absorbed by the intestine.

The absorption of NADH by the intestine was confirmed by administering a 10 mg tablet orally to each of 415 patients with Parkinson's Disease. About the same number of Parkinsonian patients were treated intravenously with the same dosage of NADH. All patients treated, both orally and intravenously, exhibited an alleviation of their symptoms. The relief experienced by those patients treated orally was comparable to that which was experienced by the patients treated intravenously, and the longer term therapeutic effects also proved to be comparable.

What is claimed is:

1. A stable, ingestable and intestine-absorbable therapeutic composition comprising NADH or NADPH, or a physiologically acceptable salt thereof, and a stabilizer selected from the group consisting of $NaHCO_3$, ascorbic acid, sodium ascorbate, tocopherols, tocopherol acetates and polyvinylpyrolidone, in a pill form, said pill having an outer surface covered by an acid stable protective coating.

2. The therapeutic composition according to claim 1 wherein the composition is in a pill form selected from the group consisting of tablet form, capsule form, microtablet form and micropellet form.

3. The therapeutic composition according to claim 1 wherein the stabilizer is selected from the group consisting of: $NaHCO_3$; sodium ascorbate; topopherol-acetates; and polyvinylpyrolidone.

4. The therapeutic composition according to claim 1 further comprising a filler.

5. The therapeutic composition according to claim 4 wherein the filler is selected from the group consisting of mannitol, microcrystalline cellulose, carboxymethyl cellulose, and dibasic calcium phosphate.

6. The therapeutic composition according to claim 1 having the following formulation: about 3 to 10% by weight NADH or NADPH; or a combination of NADH and NADPH; about 1 to 10% by weight stabilizer; and a remainder of filler.

7. The therapeutic composition according to claim 5 having the following formulation: about 3 to 10% by weight NADH or NADPH; or a combination of NADH and NADPH; about 1 to 10% by weight stabilizer; and a remainder of filler.

8. The therapeutic composition according to claim 1 wherein the coating includes a protein.

9. The therapeutic composition according to claim 1 wherein the coating includes cellulose acetate phthalate.

10. The therapeutic composition according to claim 9 wherein the coating further includes ethyl phthalate.

11. The therapeutic composition according to claim 1 characterized by having a dissolution time of at least about 2 hours in a normal stomach environment.

* * * * *